(12) United States Patent
Baumgartner et al.

(10) Patent No.: US 8,092,540 B2
(45) Date of Patent: *Jan. 10, 2012

(54) IMPLANT COMPRISING A TWO-PIECE JOINT

(75) Inventors: Daniel Baumgartner, Oesingen (CH); Adrian Burri, Bubikon (CH); Claude Mathieu, Zurich (CH)

(73) Assignee: Synthes USA, LLC, West Chester, PA (US)

( * ) Notice: Subject to any disclaimer, the term of this patent is extended or adjusted under 35 U.S.C. 154(b) by 11 days.

This patent is subject to a terminal disclaimer.

(21) Appl. No.: 12/425,005

(22) Filed: Apr. 16, 2009

(65) Prior Publication Data

US 2009/0204217 A1 Aug. 13, 2009

Related U.S. Application Data

(63) Continuation of application No. 10/528,081, filed on Mar. 15, 2005, now Pat. No. 7,537,614.

(51) Int. Cl.
*A61F 2/44* (2006.01)
(52) U.S. Cl. .................................................. 623/17.15
(58) Field of Classification Search ..... 623/17.11–17.16
See application file for complete search history.

(56) References Cited

U.S. PATENT DOCUMENTS

| | | | |
|---|---|---|---|
| 5,314,477 A | 5/1994 | Marnay | |
| 5,405,400 A | 4/1995 | Linscheid et al. | |
| 5,645,605 A | 7/1997 | Klawitter | |
| 5,895,428 A | 4/1999 | Berry | |
| 5,989,291 A | 11/1999 | Ralph et al. | |
| 6,039,763 A | 3/2000 | Shelokov | |
| 6,106,557 A * | 8/2000 | Robioneck et al. | 623/17.15 |
| 6,290,726 B1 | 9/2001 | Pope et al. | |
| 6,296,664 B1 | 10/2001 | Middleton | |
| 6,368,350 B1 | 4/2002 | Erickson et al. | |
| 6,517,580 B1 | 2/2003 | Ramadan et al. | |
| 6,540,785 B1 | 4/2003 | Gill et al. | |
| 6,610,092 B2 | 8/2003 | Ralph et al. | |
| 6,610,093 B1 | 8/2003 | Pisharodi | |
| 6,656,224 B2 | 12/2003 | Middleton | |
| 6,679,915 B1 | 1/2004 | Cauthen | |
| 6,682,561 B2 | 1/2004 | Songer et al. | |
| 6,682,562 B2 | 1/2004 | Viart et al. | |
| 6,685,742 B1 | 2/2004 | Jackson | |
| 6,706,068 B2 * | 3/2004 | Ferree | 623/17.11 |
| 6,740,118 B2 | 5/2004 | Eisermann et al. | |
| 6,764,515 B2 | 7/2004 | Ralph et al. | |
| 6,770,095 B2 | 8/2004 | Grinberg et al. | |

(Continued)

FOREIGN PATENT DOCUMENTS

CA 2 391 330 1/2001

*Primary Examiner* — David Isabella
*Assistant Examiner* — Ann Schillinger
(74) *Attorney, Agent, or Firm* — Stradley Ronon Stevens & Young, LLP

(57) ABSTRACT

An implant, in particular an intervertebral implant, comprising (A) two articulating parts (4; 5) having each a central axis (1; 26), each a curved slide surface (6; 7) intersecting the central axes (1; 26), and each an axially outermost end (14; 15) that can be connected to a bone, where (B) the slide surfaces (6; 7) are curved and displaceable one on the other, where (D) the second articulating part (5) is rotatable about two mutually skewed axes of rotation (10; 11) relative to the first articulating part (4).

16 Claims, 6 Drawing Sheets

U.S. PATENT DOCUMENTS

Figure 1:
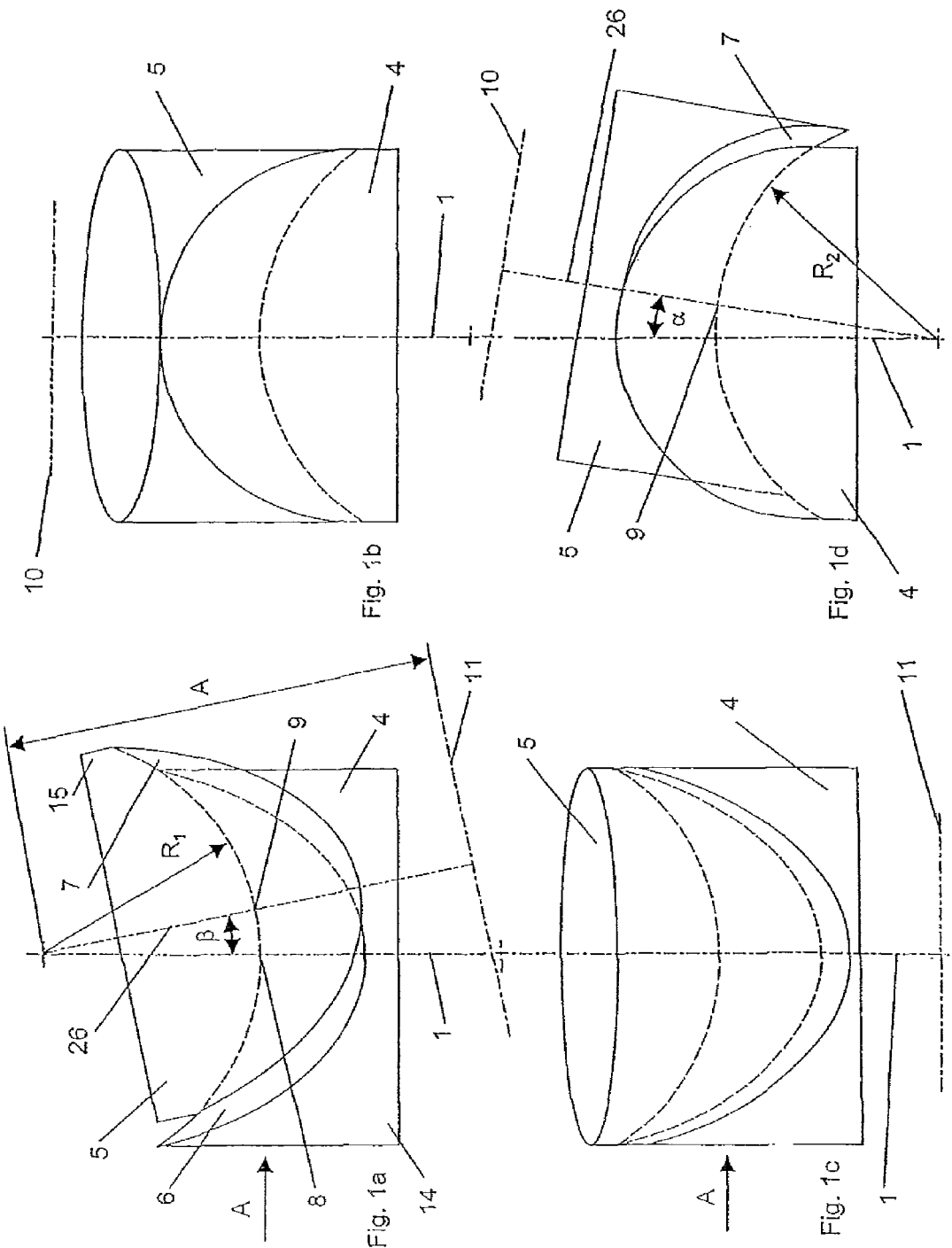

| | | |
|---|---|---|
| 6,887,274 B2 | 5/2005 | Ralph et al. |
| 6,936,071 B1 | 8/2005 | Marnay et al. |
| 7,160,327 B2 | 1/2007 | Errico et al. |
| 7,169,182 B2 | 1/2007 | Errico et al. |
| 7,179,294 B2 | 2/2007 | Eisermann et al. |
| 7,204,852 B2 | 4/2007 | Marnay et al. |
| 7,537,614 B2 * | 5/2009 | Baumgartner et al. .... 623/17.15 |
| 2004/0010316 A1 | 1/2004 | William et al. |
| 2004/0024462 A1 | 2/2004 | Ferree et al. |
| 2004/0153157 A1 | 8/2004 | Keller |

* cited by examiner

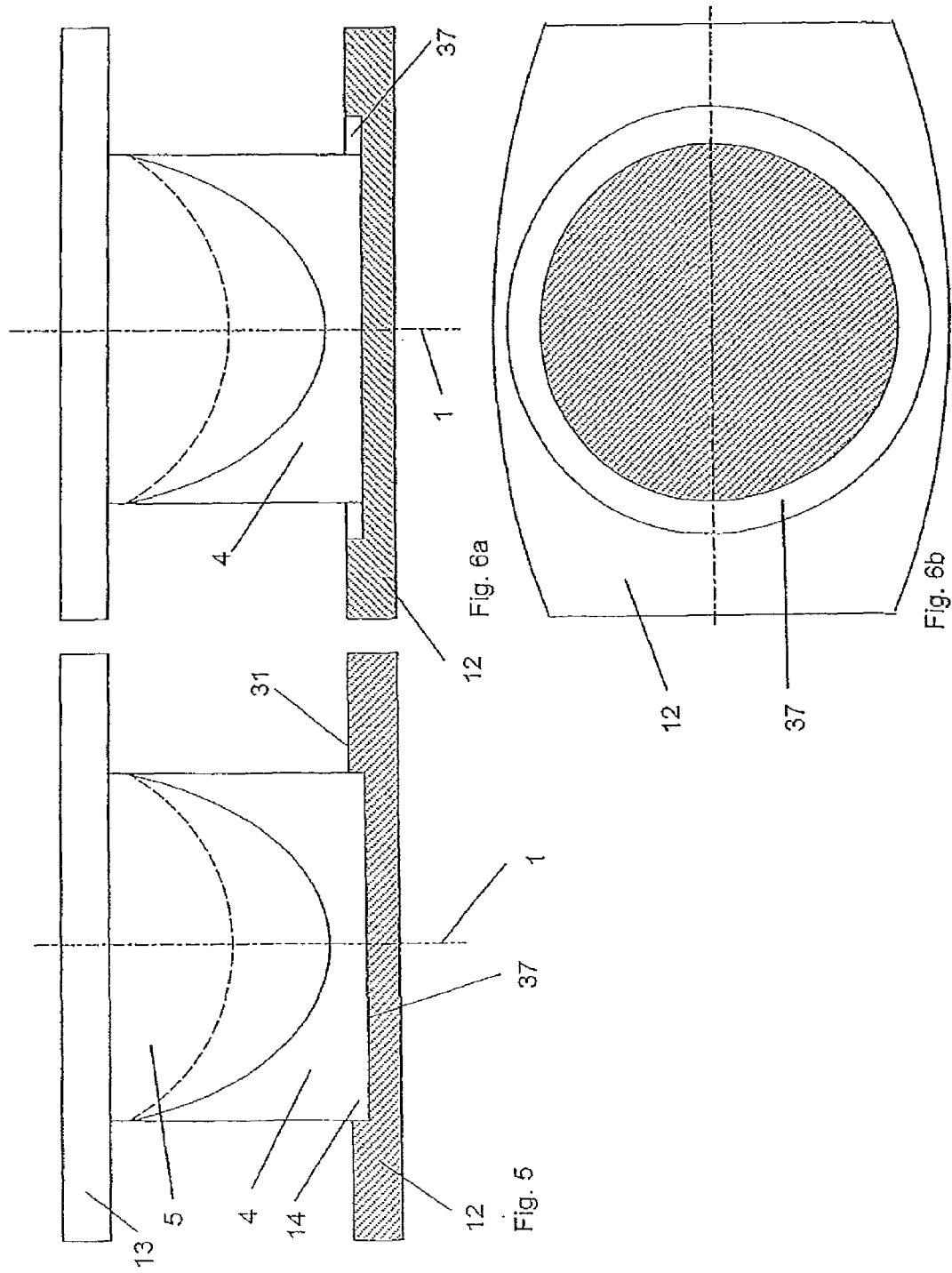

IMPLANT COMPRISING A TWO-PIECE JOINT

CROSS-REFERENCE TO RELATED APPLICATIONS

This application is a continuation of United States patent application Ser. No. 10/528,081, filed on Mar. 15, 2005, entitled "IMPLANT COMPRISING A TWO-PIECE JOINT", which claims the benefit of International Application No. PCT/CH02/00512, filed on Sep. 18, 2002, entitled "IMPLANT COMPRISING A TWO-PIECE JOINT". The entire disclosure of these applications is incorporated herein by reference.

The present invention relates to an implant, in particular an intervertebral implant defined in the preamble of claim 1.

As regards individual human body joints, for instance the joint between the distal femur condyle and the patella, or between the metacarpalia and the distal phalange, there are articulation surfaces allowing a preferred articulation about one or several joint axes while on the other hand restricting articulation about all other spatially possible axes or rotation or precluding them entirely. Implants having a joint of several axes of rotation on the other hand also are used as intervertebral implants or intervertebral disk endoprostheses.

Conventionally one or more damaged natural vertebral disks, also a damaged vertebral disk nucleus, will be removed and be partly replaced by implants or prostheses inserted into the intervertebral space between the two adjacent vertebras. The purpose is to restore conditions that shall be as natural as possible, that is, in particular the original intervertebral disk height and hence the original spacing between the two adjacent vertebras. Hopefully the vertebras' displacements take place henceforth within their natural range of excursions without being degraded by the implant or prosthesis. Such requirement entails achieving displaceabilities within the natural limits on leaning forward or backward, namely bending or stretching the spinal column as well as laterally bending the vertebras. Also a spatial change in position of the adjacent vertebras relative to one another shall be feasible within the ranges of physiological displacements.

U.S. Pat. No. 6,368,350 (Erickson) discloses an implant replacing a vertebral disk. This known implant substantially includes two articulating parts with end plates. In one embodiment mode, this joint consisting of a convex articulating part and of a complementary concave articulating part comprises spherical surfaces of articulation, as a result of which the articulating parts may be rotated about different axes of rotation that are situated in one plane, no restriction on an axis of rotation of lateral vertebral bending and on a further axis of rotation for vertebral bending/stretching taking place. Moreover rotation of the adjoining vertebras about their longitudinal axis is possible in unrestricted manner. In another embodiment mode, the articulation surfaces are the surfaces of an ellipsoid, as a result of which the axes of rotation again will not be restricted to an axis of rotation of lateral vertebral bending and to a further axis of rotation of bending/stretching the vertebras.

The object of the present invention is palliation of the above state of the art. The objective is to create an implant having two articulating articulating parts, said implant comprising two axes of rotation configured skewed to each other and spatially a defined distance apart, as a result of which, following resection of the in-between vertebral disk, the displacements of the adjacent vertebras shall be reproduced.

The present invention solves the above problem by means of an implant, preferably an intervertebral implant exhibiting the features of claim 1.

Essentially the implant of the present invention comprises two articulating parts with mutually articulating slide surfaces that, upon rotation of the articulating parts, move relative to each other Each articulating part comprises a central axis substantially parallel to or coaxial with to the longitudinal axes of two adjoining bones, said longitudinal and central axes coinciding in the rest position when the body is kept correspondingly erect, that is when the articulating parts are not mutually oblique. Moreover the articulating parts each comprise an axially outermost end that can be connected to a bone. When the implant is designed in the form of an intervertebral implant, said ends can be connected to the adjoining vertebras. The slide surfaces intersect the central axes of the articulating parts and will move relative to each other when the articulating parts rotate, the second articulating part being rotatable about two mutually skewed axes of rotation relative to the first articulating part.

In the following discussion, the first articulating part is assumed stationary and the second articulating part is assumed displaceable. As a result other axes of rotation are displaceable relative to the first articulating part and are stationary relative to the second articulating part.

Essentially the following advantages are offered by the implant, in particular the intervertebral implant of the present invention;
 the position of the center of rotation during bending or stretching and/or when laterally bending the vertebras is better matched to physiology,
 the slide surfaces can be displaced relative to and on each other in the absence of substantial friction, and forces and torques are minimized as much as possible by reproducing the corresponding lever arms, and
 twisting motions about the spinal column's longitudinal axis may be opposed by bracing.

The slide surfaces of the preferred embodiment of the implant of the invention are saddle-shaped and comprise each a saddle point. The saddle-shaped slide surfaces are designed in a manner that two surface points may be found in the vicinity of a surface point P bounded by the articulating part's dimensions so that said surface points shall be situated on different sides of the tangential plane through the surface point P.

In a further embodiment mode of the embodiment mode of the invention, the axes of rotation cross one another at angle preferably between 80 and 100°. This feature offers the advantage that, illustratively, an intervertebral implant can be implanted in a manner that one of the axes of rotation runs parallel to or coaxially with axis of the laterally bending vertebras and the other axis of rotation runs parallel to or coaxially with the axis of vertebral bending or stretching.

In another embodiment of the implant of the invention, the axes of rotation are apart by a minimum distance A between 0.1 and 20 mm, preferably between 2 and 20 mm. In part the distance A is also determined by the site of application of the implant of the invention at the spinal column and it depends according to segment height in the lumbar spinal column, decreasing in the direction of the thoracic vertebras.

Preferably the slide surfaces are designed in a manner that upon rotation of the second articulating part about each of the axes of rotation, the second saddle point moves along the arc of circle concentric with the axes of rotation. The saddle-shaped design of the slide surfaces offers the advantage of also allowing rotating the articulating parts about the central axis of these parts. However, when the articulating parts rotate axially relative to each other, said two articulating parts move axially away from one another, and as a result axial rotation is possible only if there is simultaneous change in implant height. Because of the constant prestressing force in the ligaments, muscles and sinews in the spinal column, the articulating parts can rotate axially only to a limited degree. This feature applies similarly in the lumbar spinal column to the physiological case on account of the rotation of the rear elements such as facetted joints, that allow only limited axial rotation.

Viewed in the rest condition of the articulating parts, the slide surfaces preferably shall be congruent. By designing the implant of the invention to have congruent slide surfaces, this invention precludes vertebral twisting about the spinal column's longitudinal direction unless there be a change in the height of the intervertebral implant. Changing the intervertebral implant height during such a displacement, the ligaments will be tensioned, resulting in opposition to vertebral twisting.

In a further embodiment mode of the implant of the present invention, each of the outermost ends of the articulating parts comprises a connection element that can be connected to the adjoining bone or vertebra. When the implant of the present invention is an intervertebral implant, said connection elements preferably are cover plates each having an axially outermost surface transverse to the central axes, said surfaces being fitted with a three-dimensional topography, for instance serrations or fins.

In this design furthermore one of the cover plates may be integral with the adjoining articulating part.

In one embodiment mode of the implant of the present invention in the form of an intervertebral implant, one of the cover plates comprises a guide, or groove, perpendicular to the central axis of the adjoining articulating part and insertable into the adjoining articulating part's rear end which is complementary to said guide. This feature offers the advantage first that the two cover plates resting against the first articulating part may jointly be moved between the adjacent vertebras, next that the over plates can be pressed against the end surfaces of the adjoining vertebras and that only in the end the second articulating part may be inserted between the first articulating part and the second cover plate, as a result of which the vertebras only need be under minimal traction during implantation. The second, inserted, articulating part is affixed, following insertion, to the second cover plate.

Depending on application, the articulating parts may be metal/metal pairs. Moreover ceramics also may be appropriately used, shocks will only slightly load the articulating parts because of the high prestressing forces in the spinal column between the adjoining vertebras.

In a further embodiment mode of the implant of the present invention, one of the articulating parts is made of plastic, as a result of which:

known performance-tested combinations of joint replacement materials such as highly crosslinked polyethylene (UHMWPE [ultra-high molecular weight polyethylene]) and a cobalt/chromium alloy may be used,
  low friction when the slide surfaces are moved relative to each other can be attained, and
  the rotations of the articulating parts about the central axes can be damped.

In yet another embodiment mode of the implant of the present invention, one of the articulating parts may be received at the pertinent connection element, respectively the pertinent cover plate, so as to be rotatable about its central axis. Illustratively the outermost end of the articulating part may rest in a complementary recess coaxial with the central axis and at the pertinent connection element, i.e. the associated cover plate. Conversely the connecting element may be fitted with an elevation coaxial with the central axis and the articulating part may be fitted with a recess. In this manner the invention offers the advantage that twisting motions of the two adjacent vertebras shall not be prevented by the implant.

In another embodiment mode of the implant of the present invention, one of the articulating parts received at the associated connecting element, i.e. the associated cover plate in a manner to be displaceable parallel to the displacement axis which is parallel to the central axis. Preferably the outermost articulating part end is terminally fitted with a widening configured coaxially with the central axis, whereas the associated connection element, i.e. the associated cover plate, encloses a recess which is complementary to the articulating part's outermost end and which is fitted with a recess to receive said widening This design of the implant of the present invention also allows one-axis shearing motions between the two vertebras adjoining the implant which does not hamper such motions. The vertebral shearing motion can be restricted by controlling the length of said cavity.

In yet another embodiment mode of the implant of the present invention, one of the articulating parts is received at the associated connection element, i.e. the associated cover plate, so as to be displaceable in a plane perpendicular to the central axis. Preferably the outermost end of the articulating part then comprises a smaller diameter than the recess at the corresponding connection element. This feature offers the advantage that shearing motions of the vertebras adjoining the implant also are feasible relative to several axes.

Further advantageous embodiment modes of the present invention are defined in the dependent claims.

The invention, and further developments of the invention, are elucidated below in relation to the partly schematic drawings of several illustrative embodiments.

Figure 2:
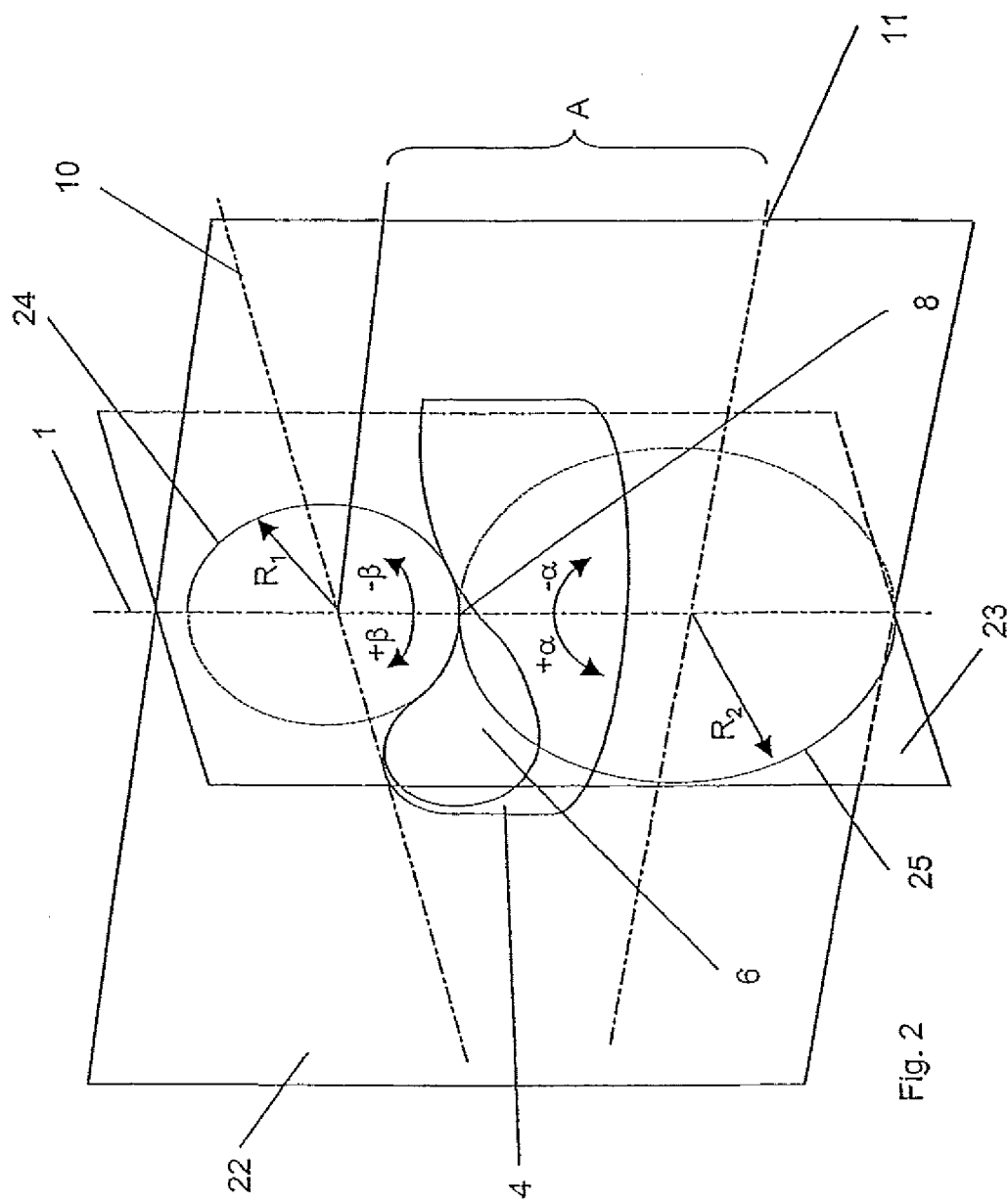
Figure 3:
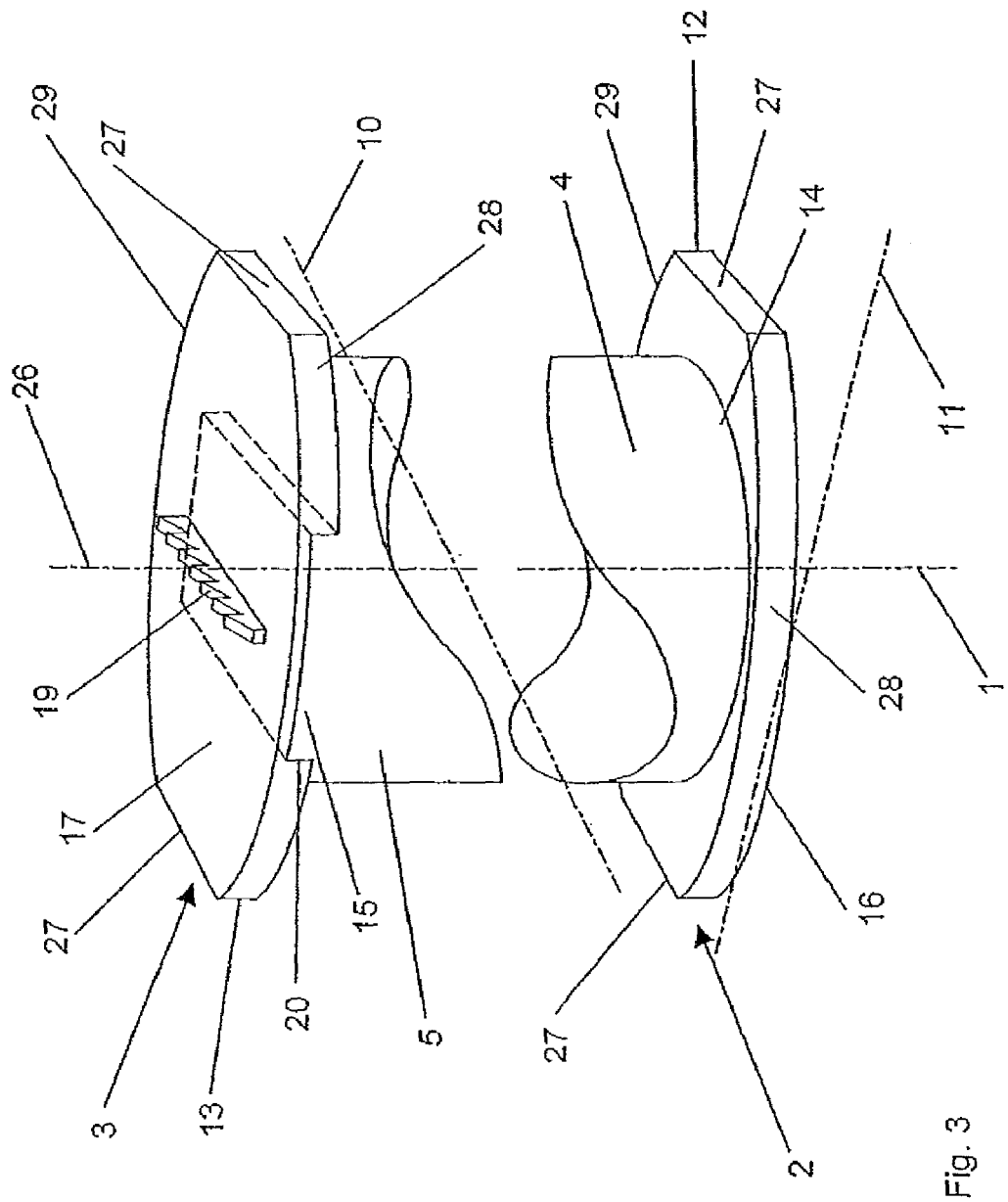
Figure 4A:
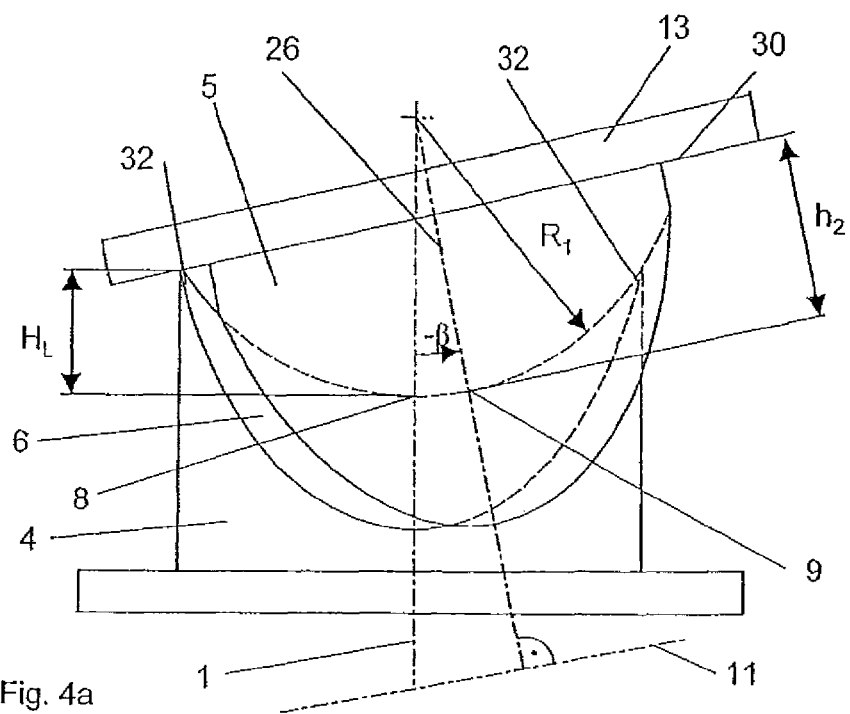
Figure 4B:
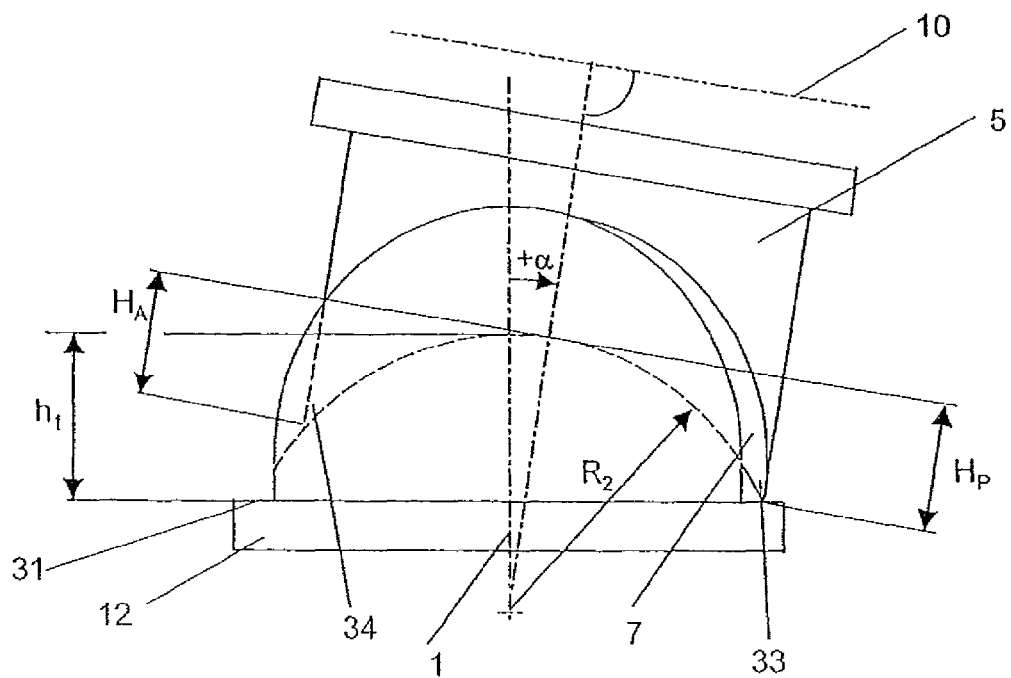
Figure 7A:
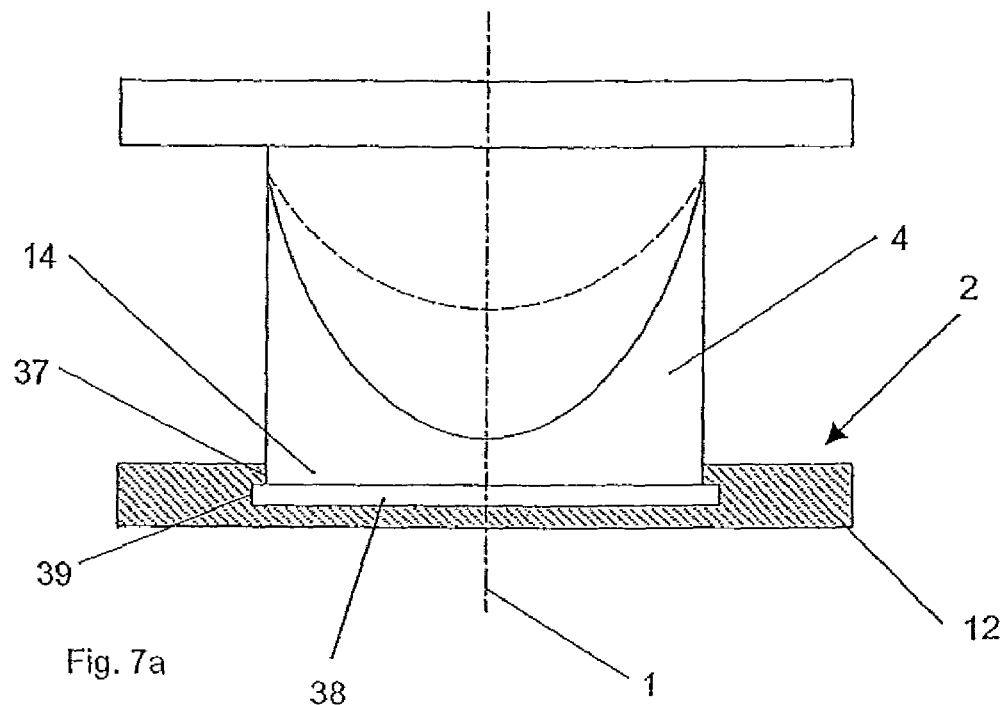
Figure 7B:
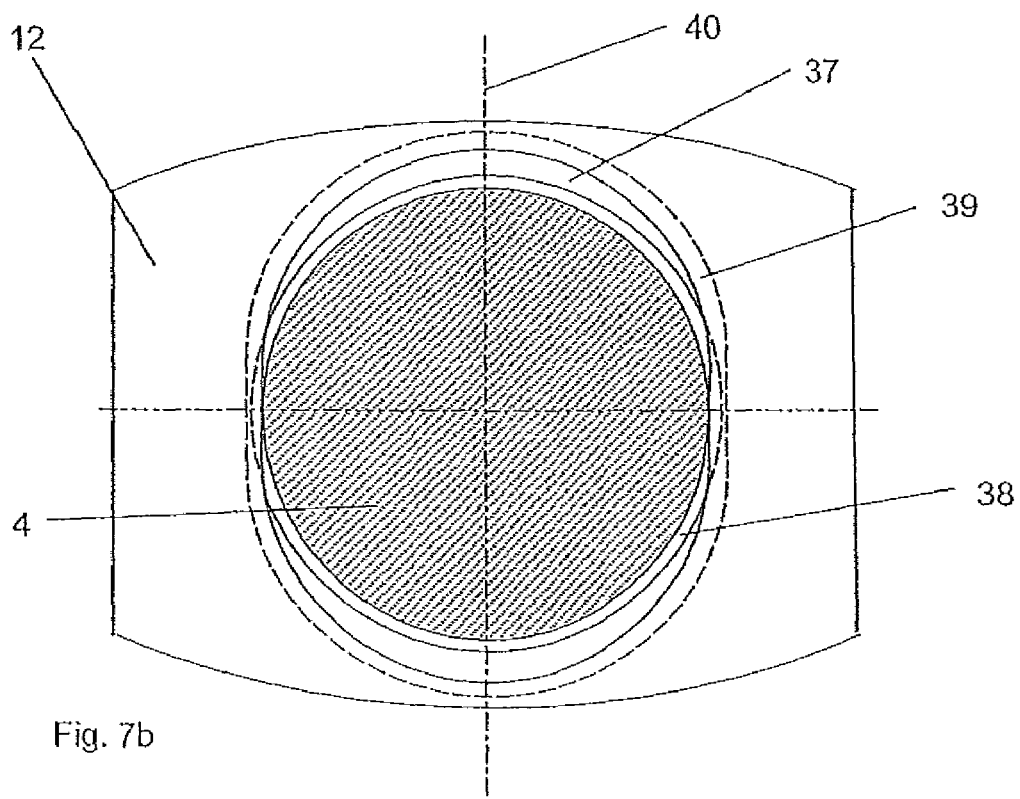

FIG. 1a is an elevation of an embodiment mode of the present implant, the second articulating part being rotated about the first axis of rotation, FIG. 1b is a sideview of the embodiment of the implant of the invention shown in FIG. 1a, FIG. 1c is a view of the embodiment of the implant of the invention shown in FIGS. 1a and 1b, the second articulating part having been rotated about the second axis of rotation, FIG. 1d is a sideview of the embodiment of the implant of the invention shown FIG. 1c, FIG. 2 is a perspective view of the articulating part of an embodiment of the implant of the invention, FIG. 3 is a perspective of an embodiment of the implant of the invention in the form of an intervertebral implant, FIG. 4a is a ventral view of an embodiment mode of the implant of the invention, FIG. 4b is a lateral view of the embodiment mode of the implant of the invention of FIG. 4a, FIG. 5 is a view of a further embodiment mode of the implant of the invention having an articulating part mounted on the cover plate and rotatable about the central axis, FIG. 6a is a view of another embodiment mode of the implant of the invention having an articulating part displaceable in a plane vertical to the central axis, FIG. 6b is a section of the embodiment mode of the implant of the invention shown in FIG. 6a, FIG. 7a is a view of a further embodiment mode of the implant of the invention having an articulating part displaceable perpendicularly to the central axis, and FIG. 7b is a section of the embodiment mode of the implant of the invention shown in FIG. 7a.

FIGS. 1a through 1d show an embodiment of the implant of the invention comprising a first and a second articulating joint 4; 5, FIG. 1b showing the two articulating parts 4; 5 in side-view A. The first articulating part 4 comprises a first central axis 1 and a first slide surface 6 intersecting said first central axis 1. Said first slide surface 6 is saddle-shaped and has a first saddle point 8. Similarly to the case of the first articulating part 4, the second articulating part 5 has a second central axis 26 and a 25 second slide surface 7 intersecting this second central axis 26. The second slide surface 7 also is saddle-shaped and includes the saddle point 9. Moreover the articulating parts 4; 5 comprise outermost ends 14; 15 which may be made to rest against the end surfaces of bones adjoining the articulating parts, in particular adjoining vertebras. The projections of the axes of rotation 10; 11 intersect in a plane orthogonal to the central axis 1 at an angle of 90°. In this design of the slide surfaces 6; 7, the minimal distance A is vertical to the two axes of rotation 10; 11. In FIGS. 1a and 1b, the second articulating part 5 has been rotated about the first axes of rotation 10 (FIG. 1b). The second saddle point 9 is displaced during the rotation of the second articulating part 5 by the angle β along an arc of circle of radius $R_1$ and concentric with the first axis of rotation 10.

FIGS. 1c and 1d show the articulating parts 4; 5 of the embodiment shown in FIGS. 1a and 1b, the second articulating part 5 having been rotated about the second axis of rotation 11 (FIG. 1c) by the angle α. During this rotation of the articulating part 5 about the second axis of rotation 11, the second saddle point 9 is displaced along an arc of circle having a radius $R_2$ concentric with the second axis of rotation 11.

FIG. 2 shows the first articulating part 4 having a saddle-shaped slide surface 6. The two axes of rotation 10; 11 are shown in the rest condition of the implant of the invention at corresponding body erectness, that is the central axis 1 of the first articulating part 4 coincides with the central axis 26 of the second articulating part 5 (FIG. 1). In the rest position, the axes of rotation 10; 11 are perpendicular to the central axis 1 and lie in the planes 22; 23. The first axis of rotation 10 runs perpendicularly to a first plane 22 which is defined by the central axis 1 and the second axis of rotation 11. The second axis of rotation 11 runs perpendicularly to a second plane 23 itself perpendicular to the first plane 22 and defined by the central axis 1 and the first axis of rotation 10. In the rest position, the first saddle point 8 of the first slide surface 6 is situated both on the central axis 1 and on two arcs or circle 24; 25 of which the center in the rest position of the articulating parts 4; 5 is defined by the intersection of the central axis 1 with each of the axes of rotation 10; 11. The first slide surface 6 on one hand tightly follows the first arc of circle 24 concentric with the first axis of rotation 10 and on the other hand also the second arc of circle 25 concentric with the axis of rotation 11. The radii $R_1$ of the first arc of circle 24 and $R_2$ of the second arc of circle 25 are equal when the slide surfaces 7; 8 are congruent and correspond to half the distance A between the two axes of rotation 10; 11.

The slide surface is designed in a manner to be the complementary shape of a patch of a toroidal surface.

FIG. 3 shows an embodiment of the implant of the invention in the form of an intervertebral implant. At their outermost ends 14; 15, the two articulating joints 4; 5 comprise a connection site 2; 3 for each cover plate 12; 13 having surfaces 16; 17 that are axially outermost along the central axes 1; 26 and that are configured transversely to the central axes 1; 26, said surfaces 16; 17 being movable to rest against the vertebras' end surfaces. The cover plates 12; 13 each comprise two lateral edge surfaces 27, one anterior edge surface 28 and one posterior edge surface 29, the lateral edge surfaces 27 being substantially parallel to the first axis of rotation 10. Both the anterior and the posterior edge surfaces 28; 29 are configured substantially parallel to the second axis of rotation 11. The implant is configured between the (omitted) adjoining vertebras in a manner that rotating the articulating parts 4; 5 about the first axis of rotation 10 allows laterally bending the vertebras connected to the implant, whereas rotating the articulating parts 4; 5 about the second axis of rotation 11 allows bending, respectively stretching the vertebras connected to the implant. In the embodiment of the implant of the invention being discussed here, the first cover plate 12 is rigidly joined to the first articulating part 4 whereas the second cover plate 13 comprises a guide 20 in the form of a channel which runs perpendicularly to the central axis 26 and substantially parallel to the lateral edge surfaces 27, as a result of which the second articulating part 5 together with its outermost end 15 designed to be complementary to the guide 20 can be inserted into this guide. Moreover serrations/fins 19 are present at the outermost surfaces 16; 17 of the cover plates 12; 13 to provide the primary implant stabilization at the adjoining vertebras.

The embodiment of the implant of the invention shown in FIGS. 4a and 4b differs from the embodiment of the implant of the invention shown in FIG. 3 only in that it is devoid of the serrations/fins 19 and in that the articulating parts 4; 5 are rotatable only within limited angles of rotation α and β about the axes of rotation 10; 11. FIG. 4a shows the implant ventrally, that is parallel to the axis of rotation 10, and FIG. 4b shows the implant laterally, that is parallel to the axis of rotation 11 (FIG. 4b). The limitation of the angles of rotation α and β is determined by selecting the sizes $H_L$; $H_A$; $H_P$; $R_1$ $R_2$; $h_1$ and $h_2$ at the articulating parts 4; 5, where, when the maximum angles of rotation α or β are reached, the particular ends 32; 33; 34—of the articulating parts 4; 5 —pointing toward the other articulating part 4; 5 will rest on the inner surfaces 30; 31 of the cover plate 12; 13 opposite the articulating part 4; 5, and:

$H_L$ is the height between the first saddle point 8 and the inner ends 32 of the first articulating joint 4 that point toward the second articulating joint 5;

$H_A$ is the height between the second saddle point 9 and the anterior end 34 of the articulating part 5 pointing toward the first articulating part 4;

$H_P$ is the height between the saddle point 9 and the posterior end 33 of the second articulating part 5 pointing toward the first articulating part 4;

$R_1$ is the radius of the first slide surface 6 in the first plane 22 (FIG. 2) perpendicular to the first axis of rotation 10 and containing the first saddle point 8;

$R_2$ is the radius of the second slide surface in the second plane 23 (FIG. 2) perpendicular to the second axis of rotation 11 and containing the second saddle point 9;

$h_1$ is the height between the first saddle point 8 and the inner surface 31 of the first cover plate 12; and $h_2$ is the height between the second saddle point 9 and the inner surface 30 of the second cover plate 13.

FIG. 5 shows an embodiment of the implant of the invention differing from the embodiments shown in FIGS. 1 through 4 in that the outermost end 14 of the first articulating part 4 is received in a complementary recess 37 in the cover plate 12 coaxial with the central axis as a result of which the first articulating part 4 may be rotated about the central axis I to be assembled to the cover plate 12.

FIGS. 6a and 6b show an embodiment of the implant of the invention which differs from the embodiment shown in FIG. 5 only in that the recess 37 exhibits a larger diameter toward the central axis 1 than the outermost end 14 of the first articulating part 4, as a result of which the first articulating part 4 is displaceable relative to the cover plate 12 in a plane that is perpendicular to the central axis 1.

FIGS. 7a and 7b show an embodiment of the implant of the invention which differs from the embodiment shown in FIG. 5 only in that the recess 37 is oval parallelly to a displacement axis 40 which is perpendicular to the central axis 1 and comprises a cavity 39 whereas the outermost end 14 of the first articulating part 4 terminally comprises a widening 38 coaxial with the central axis 1 entering said cavity 39, as result of which the first articulating part 4 on one hand is displaceable parallel to the displacement axis 40 and on the other hand is axially secured in position relative to the central axis 1 by the widening 38 engaging the cavity 39.

The invention claimed is:

1. An intervertebral implant for implantation between first and second vertebrae, the implant comprising:
   a first end plate having an inner side and a first bone contacting surface, the first bone contacting surface being sized and configured to contact the first vertebra, the inner side including a first articulating surface;
   a second end plate having an inner side and a second bone contacting surface, the second bone contacting surface being sized and configured to contact the second vertebra, the inner side including a second articulating surface for contacting the first articulating surface so that the first end plate can move with respect to the second end plate;
   wherein the first and second articulating surfaces are hyperbolic paraboloids shaped like a saddle.

2. The implant of claim 1, wherein the hyperbolic paraboloids of the first and second articulating surfaces are doubly-ruled surfaces.

3. The implant of claim 1, wherein at least one of the hyperbolic paraboloids opens up along an x-axis and down along a y-axis.

4. The implant of claim 1, further comprising:
   a first member located between the first and second end plates, the first member including a first end and a second end, the first end contacting the inner side of the first end plate, the second end including the first articulating surface; and
   a second member located between the first and second end plates, the second member including a first end and a second end, the first end contacting the inner side of the second end plate, the second end including the second articulating surface.

5. The implant of claim 4, wherein the first member is slidably displaceable with the first end plate.

6. The implant of claim 5, wherein the first member is sized and configured to be slidably displaced in a first direction but not in a second direction.

7. The implant of claim 4, wherein the first end plate includes a recess formed in the inner side thereof for receiving the first end of the first member.

8. The implant of claim 7, wherein the recess is oval shaped.

9. The implant of claim 4, wherein the first member is permitted to twist with respect to the first end plate.

10. The implant of claim 4, wherein the first member is permitted to rotate with respect to the first end plate.

11. The implant of claim 4, wherein the second member is fixed with respect to the second end plate.

12. The implant of claim 4, wherein the second member and the second end plate are integral with one another.

13. The implant of claim 1, wherein the first and second articulating surfaces enable the first member to articulate with respect to the second member through a limited angle of rotation.

14. The implant of claim 13, wherein the angle of limitation between the first and second members is limited by a portion of one of the first and second members contacting one of the inner sides of the first and second end plates.

15. The implant of claim 1, wherein the first member is rotatable with respect to the second member about two mutually skewed axes of rotation.

16. The implant of claim 15, wherein the two mutually skewed axis of rotation are separated by a distance A, the distance A being between 0.1 and 20 mm.

* * * * *